United States Patent
Von Novak, III et al.

(10) Patent No.: US 9,827,430 B1
(45) Date of Patent: Nov. 28, 2017

(54) INJECTED CONDUCTIVE TATTOOS FOR POWERING IMPLANTS

(71) Applicant: QUALCOMM Incorporated, San Diego, CA (US)

(72) Inventors: William Henry Von Novak, III, San Diego, CA (US); Virginia Walker Keating, San Diego, CA (US); Francesco Carobolante, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/423,171

(22) Filed: Feb. 2, 2017

(51) Int. Cl.
  *H01F 37/00*   (2006.01)
  *A61N 1/378*   (2006.01)
  *A61M 31/00*   (2006.01)
  *A61B 5/00*    (2006.01)
  *A61M 37/00*   (2006.01)
  *H02J 50/00*   (2016.01)

(52) U.S. Cl.
  CPC ............ *A61N 1/3787* (2013.01); *A61B 5/686* (2013.01); *A61M 31/002* (2013.01); *A61M 37/0076* (2013.01); *H02J 50/00* (2016.02); *A61B 2560/0219* (2013.01); *A61M 2205/04* (2013.01); *A61M 2205/3523* (2013.01); *A61M 2205/8206* (2013.01); *A61M 2205/8243* (2013.01); *A61M 2210/04* (2013.01)

(58) Field of Classification Search
  CPC ............................... H02J 50/00; A61N 1/3787
  See application file for complete search history.

(56) References Cited

U.S. PATENT DOCUMENTS

| | | |
|---|---|---|
| 5,715,837 A | 2/1998 | Chen |
| 2005/0061198 A1 | 3/2005 | Khan et al. |
| 2008/0303480 A1 | 12/2008 | Prutchi et al. |
| 2009/0157145 A1 | 6/2009 | Cauller |
| 2012/0045918 A1 | 2/2012 | Litzler et al. |
| 2013/0241306 A1 | 9/2013 | Aber et al. |
| 2013/0310629 A1 | 11/2013 | Lafontaine |
| 2014/0336724 A1 | 11/2014 | Ng et al. |
| 2015/0080639 A1 | 3/2015 | Radziemski et al. |

(Continued)

FOREIGN PATENT DOCUMENTS

WO    2012170278 A2    12/2012

OTHER PUBLICATIONS

Kim et al., Epidermal Electronics, Aug. 2011, Science, vol. 12, pp. 838-843.*

(Continued)

*Primary Examiner* — Daniel Cavallari
(74) *Attorney, Agent, or Firm* — Colby Nipper

(57) ABSTRACT

The present disclosure describes aspects of injected conductive tattoos for powering implants. In some aspects, a system comprises a conductive tattoo used to efficiently transfer power wirelessly received from a transmitter outside a body to an electronic device in the body. The conductive tattoo is formed from a conductive material injected into an outermost permanent layer of the body. The conductive tattoo is configured to wirelessly receive and relay the power from the transmitter to the electronic device. In particular, the conductive tattoo may transfer the power to the electronic device over a coupling between the conductive tattoo and the electronic device.

30 Claims, 12 Drawing Sheets

(56) References Cited

U.S. PATENT DOCUMENTS

2015/0229134 A1 8/2015 Masaoka et al.
2015/0290379 A1 10/2015 Rudser et al.
2015/0321000 A1* 11/2015 Rosenbluth .......... A61N 1/0492
607/48

OTHER PUBLICATIONS

Bandodkar A.J., et al., "Tattoo-Based Wearable Electrochemical Devices: A Review", Electro Analysis, vol. 27, No. 3, Jan. 8, 2015, pp. 562-572.
Co-pending U.S. Appl. No. 15/267,639, filed on Sep. 16, 2016.
International Search Report and Written Opinion — PCT/US2017/020123 — ISA/EPO — Jun. 9, 2017 (162190WO).

* cited by examiner

INJECTED CONDUCTIVE TATTOOS FOR POWERING IMPLANTS

FIELD OF THE DISCLOSURE

This disclosure relates generally to wirelessly charging an implant within a body. More particularly, the disclosure relates to utilizing an injected conductive tattoo to power an implant.

BACKGROUND

This description of related art is provided for the purpose of generally presenting a context for the disclosure that follows. Unless indicated otherwise herein, concepts described in this section are not prior art to this disclosure and are not admitted to be prior art by inclusion herein.

Biomedical implants are becoming more common for treatment of disease and medical conditions in humans as well as in animals. These implants can be inserted into a host's body for a variety of purposes, such as to release metered doses of medication, stimulate bodily tissue (e.g., nerves), monitor specific biochemical conditions, and so on. Oftentimes, such implants require electrical energy in order to operate—they need a power source, which typically takes the form of a chemical battery. Although implants are expected to be operative for several years (or a host's lifetime) without replacement, the chemical batteries used to power them may not be capable of operating that long. Thus, to keep these implants operating as designed, their batteries may need to be changed. Changing chemical batteries that are implanted can be difficult, however, and doing so can pose a significant risk to the host. Accordingly, conventional techniques for powering implants can put a host's life at risk.

SUMMARY

In some aspects of injected conductive tattoos for powering implants, a system uses a conductive tattoo to transfer power wirelessly received from a transmitter outside a body to an electronic device in the body. The conductive tattoo is formed from a conductive material injected into an outermost permanent layer of the body. The conductive tattoo is configured to wirelessly receive and relay the power from the transmitter to the electronic device. In particular, the conductive tattoo may transfer the power to the electronic device over a coupling between the conductive tattoo and the electronic device.

Some aspects of injected conductive tattoos for powering implants also involve a method in which power is wirelessly received from a transmitter by a conductive tattoo applied within a body's skin. The method also comprises transferring the power from the conductive tattoo to an electronic device within the body.

In other aspects, a method for injected conductive tattoos for powering implants comprises forming conductive particles from a conductive material. The method also includes suspending the conductive particles in a solution to produce a conductive solution. The conductive solution can then be transferred to a tattoo machine. Further, the method comprises applying the conductive solution into skin of a body in a pattern to form a conductive tattoo. The conductive particles disposed in the pattern enable the conductive tattoo to receive power transmitted wirelessly from the transmitter and transfer the power to the electronic device.

In some aspects, an implant in a body can be powered using a system that transfers power wirelessly from outside the body. The system includes a power-transferring means for transferring power wirelessly transmitted by a transmitter means outside the body to a power-receiving means in the body. In aspects, the power-transferring means is embedded in an outermost permanent layer of the body. The system also includes implant-function means for carrying out corresponding functionality of the implant in the body using the power transferred to the power-receiving means.

BRIEF DESCRIPTION OF DRAWINGS

The details of various aspects are set forth in the accompanying figures and the detailed description that follows. In the figures, the left-most digit of a reference number identifies the figure in which the reference number first appears. The use of the same reference numbers in different instances in the description or the figures indicates like elements.

DETAILED DESCRIPTION

Figure 1:
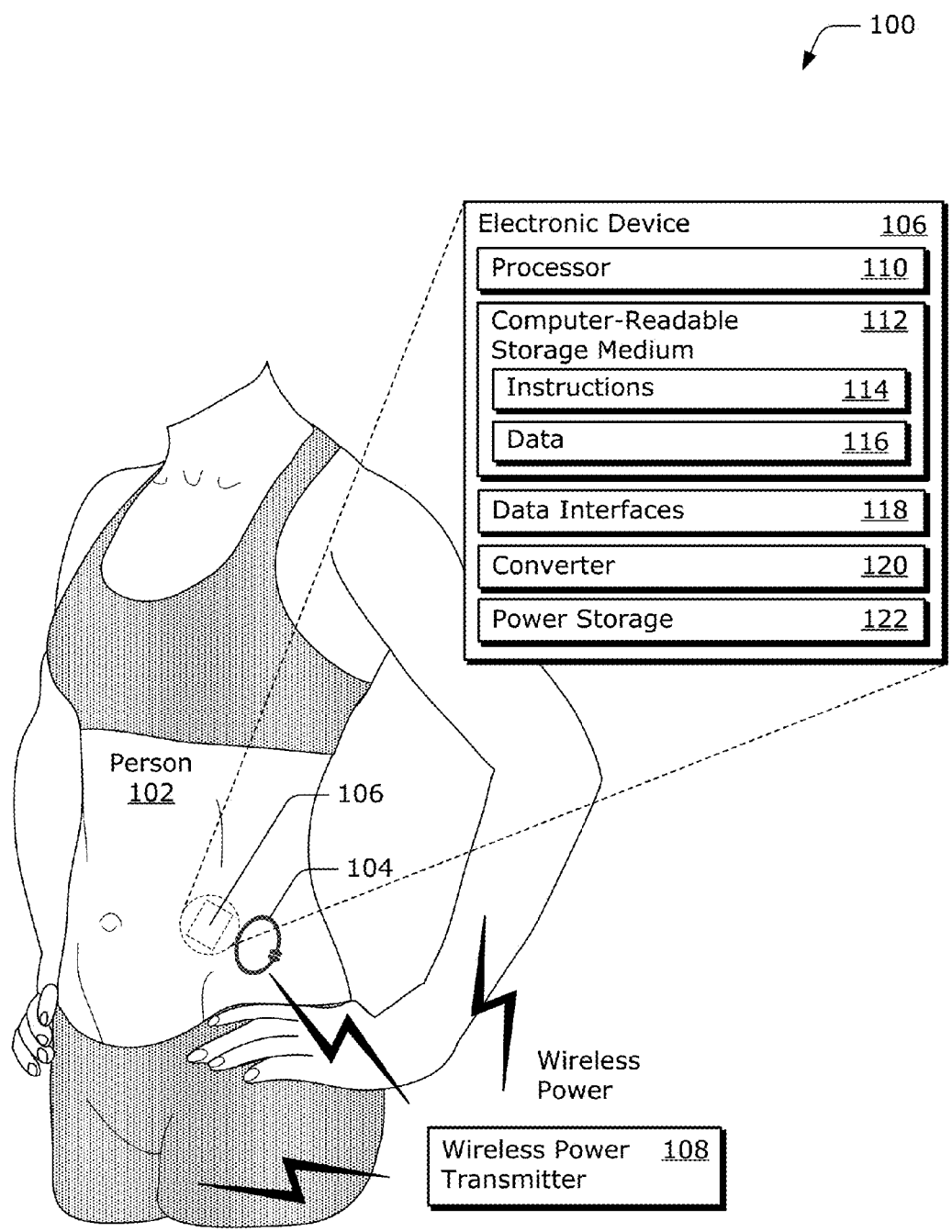
FIG. 1 illustrates an example environment that includes an injected conductive tattoo.

Devices implanted in humans and animals are becoming more common, such as biomedical implants capable of treating disease and medical conditions. As used herein, a "host" refers to a respective body (e.g., human or animal) in which an implant is surgically inserted. Biomedical implants can be inserted into a host's body for a variety of purposes, such as to release metered doses of medication, stimulate bodily tissue (e.g., nerves), monitor specific biochemical conditions, and so on. Many implants (biomedical or otherwise) often require electrical energy in order to operate. In other words, these implants need a power source. Often the power source used to power an implant is a chemical battery. Broadly speaking, implants are capable of operating for several years (or a host's entire lifetime) without replacement. The chemical batteries used to power these implants, however, often are not capable of providing power that long.

Thus, to keep an implant operating as designed, its battery may need to be surgically changed. The surgical procedures for changing implanted chemical batteries can be invasive and difficult to perform, however. Furthermore, doing so can pose a significant risk to the host. Accordingly, conventional techniques for powering implants can put a host's life at risk.

This disclosure describes aspects of utilizing injected conductive tattoos for powering implants. The apparatuses and methods described herein power implants within a body using power received by an injected conductive tattoo in the body's skin. In particular, aspects involve tattooing conductive particles into an implant host's skin to form the conductive tattoo. Aspects also involve receiving power at the conductive tattoo from a wireless power transmitter located outside the body and providing the power from the conductive tattoo to an implant via a coupling, e.g., a wired or wireless coupling.

Injected conductive tattoos are used to achieve high couplings with power transmitters outside a host's body. Some techniques may involve transmitting power from a wireless power transmitter outside a body directly to a power-receiving device within the body, e.g., a receiver of an implant. Due at least in part to a difference in transmission mediums within and outside the body, however, power loss may occur with such techniques. Further, the amount of power loss observed may increase for implants deeper within the body. In contrast, the described aspects involve injecting a conductive tattoo just under the skin to achieve higher coupling with external resonators (e.g., transmit antennas) placed just above the skin.

Like standard ink tattoos, the conductive material of the described conductive tattoos is injected into the skin, including into the first permanent layer of the skin. This first permanent layer is the outermost permanent layer of the body and thus provides a closest coupling of a permanent fixture within the body without repeatedly or permanently breaking the skin, which can leave an opening for infection.

Once the particles of the conductive material are injected, the body encases these particles with specialized dermal cells called fibroblasts. The fibroblasts keep the particles in place within the skin, preventing them from being carried away by the lymph system. In addition, some particles are encapsulated and held in the dermis by specialized immune system cells called macrophages. This is the same biological process that keeps ink of a conventional, decorative tattoo in place. When securely in place, the particles of the conductive material can couple with a transmitter placed at the surface of the skin.

In particular, the conductive particles of the injected conductive tattoos described herein may be configured as wireless power resonators when exposed to a wireless field generated by external resonators. As discussed with reference to FIGS. 5-6, the conductive particles can be injected into the skin in a pattern that allows the injected conductive tattoo to form structures with capacitance—in other words the pattern allows the injected conductive tattoo to store and carry electrical charge (e.g., and therefore form a resonant structure with inductance and capacitance). The power received by the injected conductive tattoo can then be transferred to implants within the body.

In some aspects, an injected conductive tattoo may be wirelessly coupled to the implant. In these scenarios, the injected conductive tattoo receives power wirelessly from an external transmitter and then retransmits the power through the body to the implant. An advantage of utilizing the injected conductive tattoo to retransmit the wireless power to the implant is a reduction in power loss relative to techniques that wirelessly transmit power directly from an external transmitter to an implant. In other words, the conductive tattoo enables wireless power to be transferred more efficiently from an external transmitter to an implant in the body. This is because the injected conductive tattoo transmits power to the implant over a substantially similar transmission medium (e.g., bodily tissue), whereas the direct transmission techniques involve transmitting power to the implant over different transmission mediums (e.g., air and then bodily tissue). Couplings between an external transmitter and internal power receiver may be lower due to impedance changes from the air to the bodily tissue, lossy transmission mediums within the body, and small receiver antenna sizes.

These and other aspects of injected conductive tattoos for powering implants are described below in the context of an example environment, example arrangements and configurations of injected conductive tattoos, and techniques. Any reference made with respect to the example environment or injected conductive tattoos, or elements thereof, is by way of example only and is not intended to limit any of the aspects described herein.

Example Environment

FIG. 1 illustrates an example environment 100, which includes a person 102 having injected conductive tattoo 104 (conductive tattoo 104) and in which an implanted electronic device 106 has been surgically inserted. The example environment also includes wireless power transmitter 108, which is configured to transmit power wirelessly to the conductive tattoo 104. The wireless power transmitter 108 may be configured as a wide field transmitter that transmits power widely or beams power narrowly from somewhere in a room. Alternately or in addition, the wireless power transmitter 108 may be configured as an antenna that is intended to be physically close to the person 102, such as placed directly on the person 102's skin as in FIGS. 3 and 4. In accordance with the aspects described herein, the conductive tattoo 104 is configured to transmit the power it receives from the wireless power transmitter 108 to the electronic device 106.

The electronic device 106 may be may be implemented as any suitable computing or electronic device that is implanted in the person 102 and capable of being powered with the wireless power received by the conductive tattoo 104 from the wireless power transmitter 108. Examples of the electronic device 106 include implants to release metered doses of medication, implants to stimulate bodily tissue (e.g., nerves), implants for treating infertility, implants to monitor specific biochemical conditions, and so on. Electronic devices other than medical-based implants may also be contemplated within the techniques described herein, such as personal communication devices, identification devices, location tracking devices, and so forth. Accordingly, the electronic device 106 may correspond to a variety of different implanted computing or electronic devices without departing from the spirit or scope of the techniques described herein.

The electronic device 106 includes a processor 110. In the example, the electronic device 106 also includes computer-readable storage medium 112 (CRM 112). The processor 110 may include any type of processor, such as an application processor or multi-core processor, configured to execute processor-executable code stored by the CRM 112. The CRM 112 may include any suitable type of data storage media, such as volatile memory (e.g., random access memory (RAM)), non-volatile memory (e.g., Flash memory), optical media, magnetic media (e.g., disk or tape), and the like. In the context of this disclosure, the CRM 112 is implemented to store instructions 114, data 116, and other information of the electronic device 106, and thus does not include transitory propagating signals or carrier waves. Further, although the electronic device 106 is illustrated with the CRM 112, in some aspects the electronic device 106 may instead or additionally be implemented using a system-on-chip (SoC) as further described in relation to FIG. 11.

In the example, the electronic device 106 also includes data interfaces 118. The data interfaces 118 provide connectivity to respective networks and other electronic devices connected therewith. The data interfaces 118 may comprise wired data interfaces (that are usable to connect with the electronic device 106 before it is implanted into a body, during a surgical procedure in which the electronic device 106 is exposed, when the electronic device 106 has been removed from the body, and so on), wireless data interfaces, or any suitable combination thereof. Alternately or additionally, the wireless interfaces may include a modem or radio configured to communicate over a wireless network, such as a wireless LAN, peer-to-peer (P2P), cellular network, and/or wireless personal-area-network (WPAN).

The electronic device 106 also includes converter 120 and power storage 122. The converter 120 converts power received from the conductive tattoo 104 via a coupling, such as a wired or wireless coupling with the conductive tattoo 104. The converter 120 is capable of converting the power into a form that is usable by the electronic device 106 to perform its corresponding functionality. By way of example, the converter 120 represents functionality to boost a voltage of the power harvested.

The power storage 122 represents functionality to store power received via the conductive tattoo 104 for later use. In some aspects, the power received from the conductive tattoo 104 may be fed to the power storage 122, and the electronic device 106 may draw power for operation from the power storage 122. In other aspects, the electronic device 106 may utilize power for operation as it is received from the conductive tattoo 104 and rely on the power storage 122 solely when the power received directly from the conductive tattoo 104 is not enough to function properly. In both cases, the electronic device 106 may be configured to use power stored in the power storage 122 for operation.

In general, the conductive tattoo 104 represents functionality of conductive particles, injected into the person 102's skin, to receive power from the wireless power transmitter 108 and retransmit the power over a coupling to the electronic device 106 in the person 102. The conductive particles may be formed from an inorganic, conductive material that is ground into particles, each having an approximate size of 13-14 microns. By way of example, the conductive material may comprise at least one of copper, gold, silver, carbon, or titanium oxide. In general, the conductive material is ground small enough to fit within a skin cell (e.g., eventually a fibroblast), but large enough not to be carried away by the lymph system. To provide some context for the approximate size of the conductive particles, lymphocytes generally have a size of 6-12 microns and fibroblasts generally have a size of 10-15 microns. Different conductive materials may be chosen to give the conductive tattoo 104 a variety of different tattoo properties, such as different colors, to tune the power received from the wireless power transmitter 108 in different manners, and so forth. In general, the conductive tattoo 104 is configured to generate a magnetic field in response to a magnetic field generated by the wireless power transmitter 108. Further, the conductive tattoo 104 may inductively couple with the electronic device 106 via the generated magnetic field to transfer power to the electronic device 106.

In one or more aspects, a band of insulating ink may be tattooed around the conductive particles to prevent migration of the conductive particles through the skin over time. The insulating ink may comprise non-conductive or minimally conductive particles, such as acrylic or latex based ink. The band of insulating ink can also serve as insulation to maintain a gap between portions of a pattern in which the conductive particles are injected to form the conductive tattoo 104. As discussed in more detail below, the pattern in which the conductive particles are injected may allow the conductive tattoo 104 to carry a capacitance.

Regardless of a material from which the conductive particles are formed, the conductive particles are injected into the first permanent layer of skin (the dermis), like ink of traditional decorative tattoos, to form the conductive tattoo 104. To the extent that the first permanent layer of skin is the outermost permanent layer of the person 102's body, it provides a closest coupling of a permanent fixture in the body to the wireless power transmitter 108. Once the conductive particles are injected, the person 102's body will respond with the biological process described above that keeps the conductive particles in place, e.g., in the pattern in which the conductive particles were injected to form the conductive tattoo 104.

In accordance with the described aspects, the conductive tattoo 104 is also coupled to the electronic device 106 to supply the electronic device 106 with power for operation. As described herein below, with reference to FIGS. 3-4, this coupling may be wired or wireless. In scenarios employing a wired coupling, a wire or conductor is surgically implanted in the person 102 to connect the conductive tattoo 104 to the electronic device 106. In scenarios employing a wireless coupling, the conductive tattoo 104 receives power from the wireless power transmitter 108. In these wireless scenarios, the power is then retransmitted wirelessly through the person 102's body for receipt by the electronic device 106. How an injected conductive tattoo 104 may be specifically implemented to power an implant in a body is described in greater detail below.

Example Injected Conductive Tattoos

Figure 2:
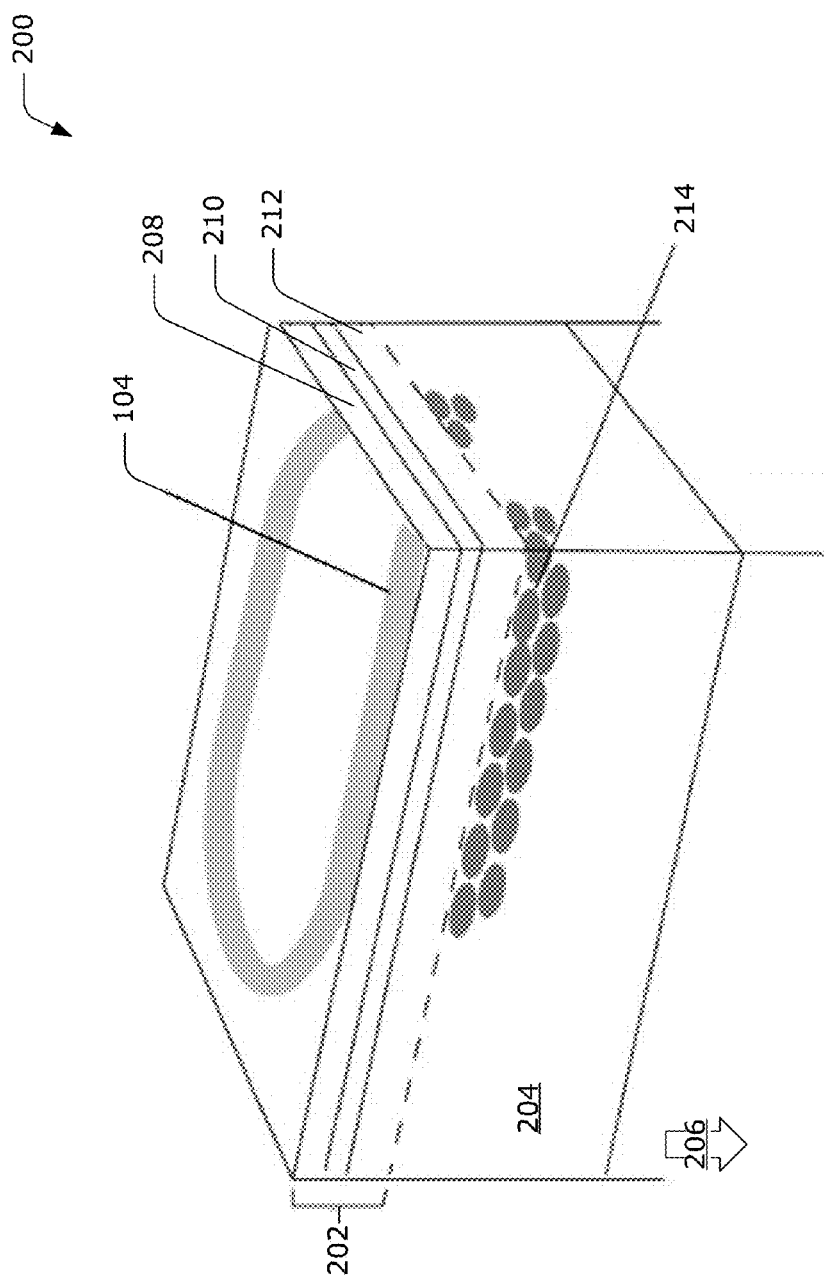
FIG. 2 illustrates an example cross-sectional view of skin with the injected conductive tattoo shown in FIG. 1.

FIG. 2 illustrates an example cross-sectional view of skin with an injected conductive tattoo 104 (conductive tattoo 104) in accordance with one or more aspects at 200. The skin in the illustrated example may correspond to human skin or the skin of an animal. The example cross-sectional view may correspond to skin of the person 102, for example. In general, the skin of both humans and animals has multiple layers, at least some of which are depicted in the example cross-sectional view of the skin at 200.

In particular, the cross-sectional view depicts skin layers including epidermis 202, dermis 204, and hypodermis 206, which is represented by an arrow. The epidermis 202 is the outermost layer of skin, but is not a permanent structure of the body. The epidermis 202 has multiple sublayers including stratum corneum 208, stratum lucidum 210, and basement membrane 212. The stratum corneum 208 is an old, outermost layer of dying skin. In accordance with the aspects described herein, the stratum corneum 208 can be scrubbed off (e.g., through exfoliation) before placing the wireless power transmitter 108 against the skin proximate the conductive tattoo 104. Removing this layer can further reduce a distance between the wireless power transmitter 108 and the conductive tattoo 104. This reduced distance can be effective to improve an efficiency of the coupling (e.g., reduce an amount of power loss) relative to scenarios in which the stratum corneum 208 is not scrubbed off. The stratum lucidum 210 is a layer of new outer skin that provides a barrier against contaminants. The basement membrane 212 has basale, spinosum, and granulosum stratum. These are newly developing skin sublayers.

In addition, FIG. 2 depicts conductive particles 214, which are injected into skin to the form the conductive tattoo 104. The conductive particles 214 may be formed for injection into the dermis 204 by grinding down an inorganic conductive material, so the resulting particles have a size of approximately 13-14 microns. Once injected, the conductive particles 214 may be set in place via the biological process discussed above. This biological process causes the conductive particles 214 to be positioned in the outermost permanent layer of the skin, the dermis 204—about 2-4 millimeters below a surface of the skin. When the stratum corneum 208 is scrubbed off though, the conductive particles 214 may be less than 2-4 millimeters from the surface of the skin. In any case, the conductive particles 214 create an area of conductivity. In some cases, the conductive particles 214 can be visible through the surface of skin, as illustrated.

In accordance with the aspects discussed herein, the conductive particles 214 can be injected in a variety of different ways, such that a size and configuration of the conductive tattoo 104 may vary widely from application to application. For example, conductive tattoos that cover larger areas may reduce current density in the skin in relation to conductive tattoos that cover smaller areas. In addition to varying in size and configuration, the conductive tattoo 104 may also vary in visibility, e.g., from appearing unnoticeable to plainly visible.

Mildly visible or unnoticeable conductive tattoos may be achieved by suspending the conductive particles 214 in a transparent solution, such as saline, water, plasma, and so forth. This mixture of the conductive particles 214 and transparent solution may then be injected into the skin to form a mildly visible or unnoticeable tattoo. In contrast, highly visible tattoos may be achieved by suspending the conductive particles 214 in a colored solution, such as black or colored decorative tattoo ink. This mixture of conductive particles 214 and colored solution may then be injected into the skin to form a visible tattoo. One advantage of a highly visible tattoo over a mildly visible or unnoticeable tattoo is that care givers and medical professionals may be able to easily find where to place the wireless power transmitter 108 to charge the electronic device 106 in emergency situations. In some scenarios, the person 102 may wish to camouflage the conductive tattoo 104. The conductive tattoo 104 can be camouflaged, for instance, by covering it with a traditional, decorative ink tattoo.

Regardless of a size, configuration, or visibility, the conductive tattoo 104 is configured to power the electronic device 106. To do so, power is initially transferred through the skin to the conductive tattoo 104. This transfer of power through the skin (e.g., from the wireless power transmitter 108) to the conductive tattoo 104 may be referred to herein as a "transcutaneous link." By leveraging the conductive tattoo 104 for the transcutaneous link, an amount of power lost when transferring power into the body may be reduced. In accordance with one or more aspects, the transfer of power from outside the body to inside is performed using low frequency or direct current (DC) power. In addition to power transfer via the transcutaneous link, power is also transferred from the conductive tattoo 104 to the electronic device 106. The power transfer between the conductive tattoo 104 and the electronic device 106 may be referred to herein as a "deep link." Example configurations that utilize the conductive tattoo 104 to power the electronic device 106 are illustrated in FIGS. 3 and 4.

Figure 3:
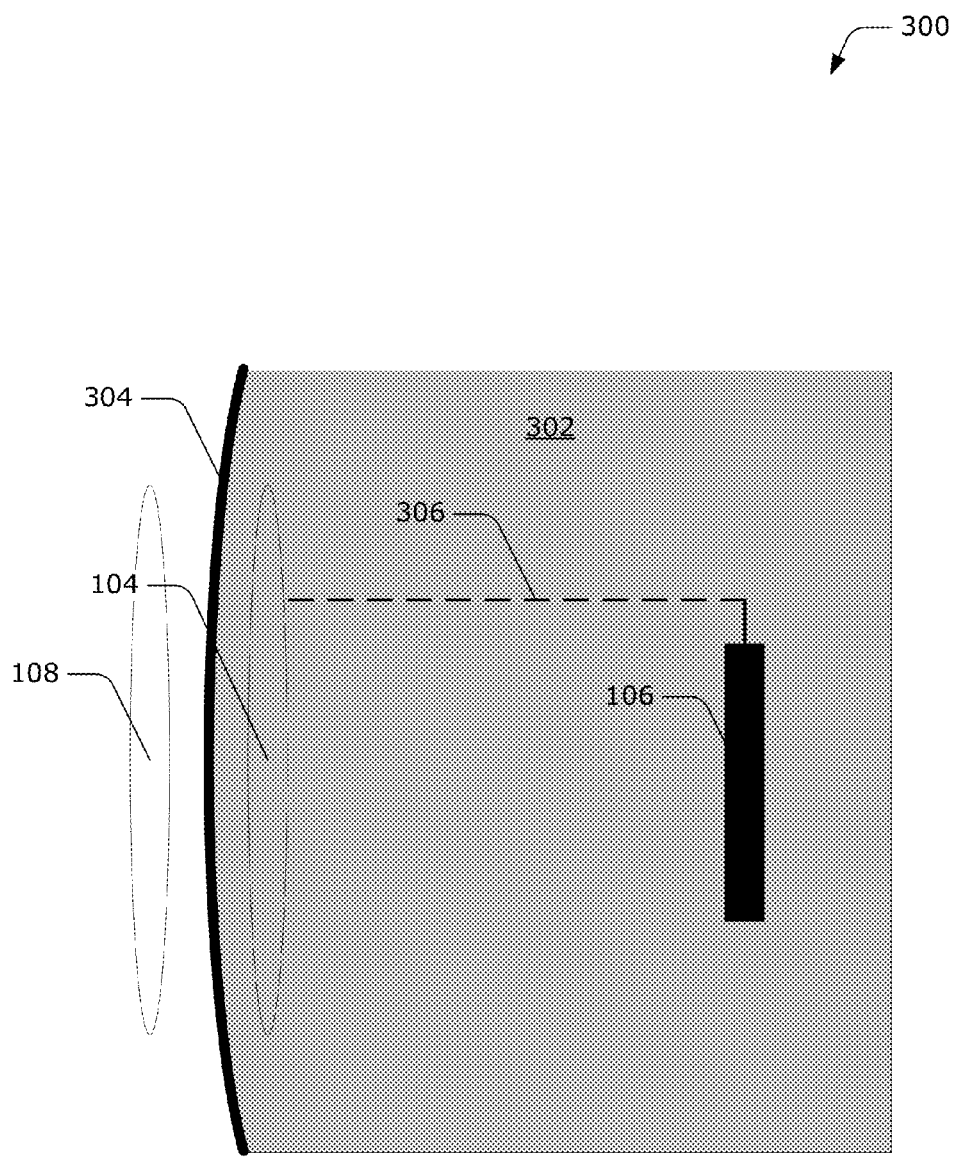
FIG. 3 illustrates an example configuration in which an injected conductive tattoo receives power wirelessly from a transmitter outside the body and is wirelessly coupled to an implanted electronic device.
Figure 4:
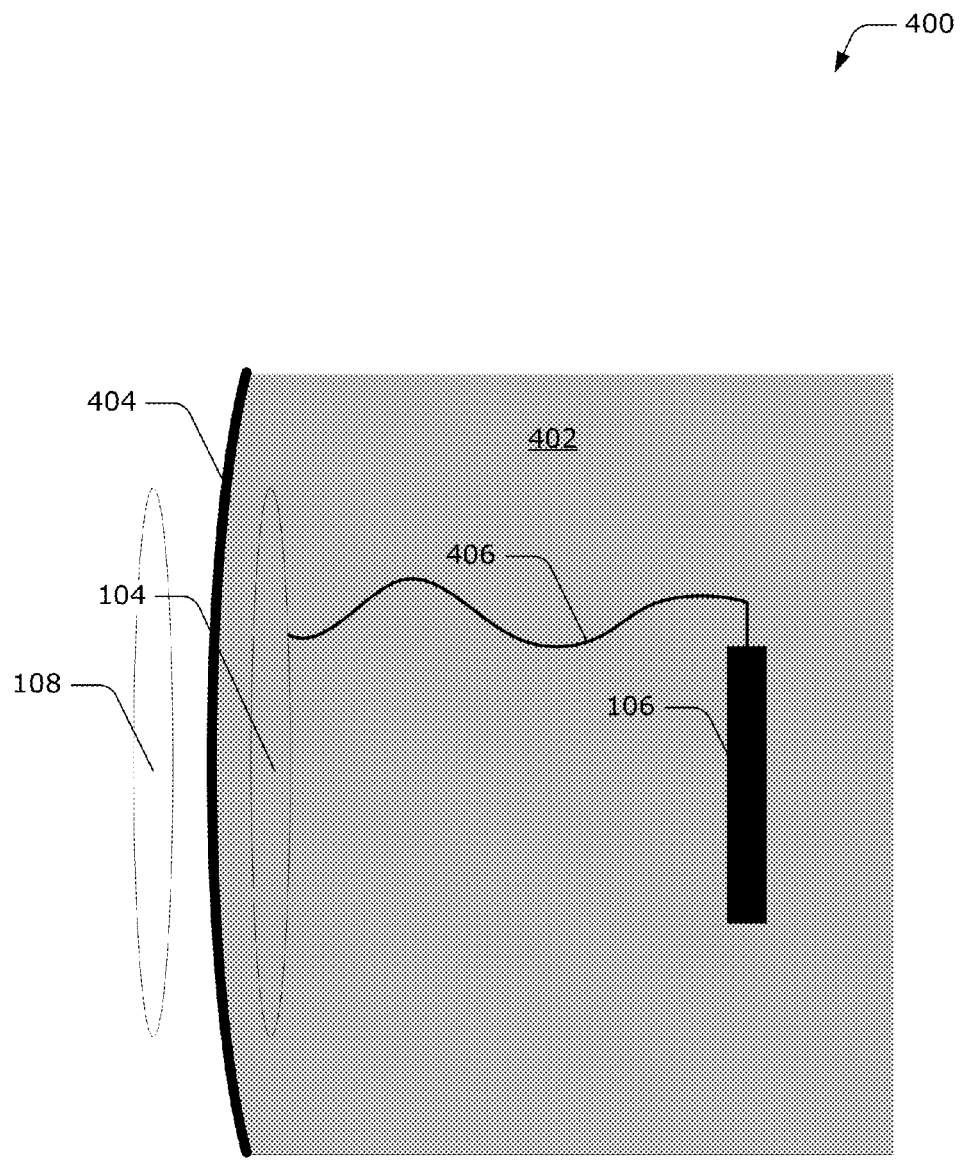
FIG. 4 illustrates another example configuration in which an injected conductive tattoo receives power wirelessly from a transmitter outside the body and has a wired coupling to an implanted electronic device.

FIG. 3 illustrates an example configuration in which an injected conductive tattoo receives power wirelessly from a transmitter outside the body and is wirelessly coupled to an implanted electronic device in accordance with one or more aspects at 300. The depicted configuration includes the conductive tattoo 104, the electronic device 106, and the wireless power transmitter 108. The depicted configuration also includes bodily tissue 302 with skin 304. It should be appreciated that some of the depicted bodily tissue 302 may also correspond to different layers of skin, e.g., between the skin 304 and the conductive tattoo 104. Additionally, the bodily tissue 302 may include other types of tissues, such as muscle, fat, tendons, ligaments, blood vessels, nerves, organs, and so forth. The bodily tissue 302 between the conductive tattoo 104 and the electronic device 106 may correspond to these different types, for instance.

With regard to the transcutaneous link, the corresponding transfer of power may occur when the wireless power transmitter 108 is placed on the skin 304 over the conductive tattoo 104. In the scenario where the conductive tattoo 104 is visible, for instance, the wireless power transmitter 108 may be placed on the skin 304 where the conductive tattoo 104 can be seen through the skin 304. After being transferred into the body, the power is carried by the conductive tattoo 104 for transfer to the electronic device 106. The power carried by the conductive tattoo 104 may be transferred to the electronic device 106 using a variety of differently configured deep links, such as over a wireless coupling and over a wired coupling.

As one example, the conductive tattoo 104 forms a resonant circuit comprising an inductor and a capacitor where the resonant circuit is configured to inductively couple to a magnetic field generated by the wireless power transmitter 108. In this example, the resonant circuit is configured to generate a magnetic field in response to the magnetic field generated by the wireless power transmitter 108. Further, a receiver coil (not shown) of the electronic device 106 is configured to inductively couple power from the magnetic field generated by the conductive tattoo 104. In this scenario, an amount of coupling by the receiver coil with a field is much higher to the wireless field generated by the conductive tattoo 104 as compared to the amount of coupling to the wireless field generated by the wireless power transmitter 108.

The example configuration depicted in FIG. 3 represents a scenario in which the deep link is implemented via wireless coupling 306. In particular, the example configuration represents a scenario in which the power received by the conductive tattoo 104, from the wireless power transmitter 108, is retransmitted to the electronic device 106 across the wireless coupling 306. The wireless coupling 306 may be achieved between the transcutaneous link and the deep link, for instance, through conversion or transformation.

In conversion-based wireless deep links, the signal is converted from received power to one of direct current (DC) power or alternating current (AC) power. Such conversion is one example of how signal characteristics—in this case a waveform—of power received by the conductive tattoo 104 can be adjusted. The signal is then converted back to a form needed for the deep link. In one or more aspects, a complete receiver circuit generates DC power, and a complete transmitter circuit re-transmits the power to the electronic device 106 via the deep link. In contrast to conversion-based wireless deep links, transformation-based wireless deep links transform rather than convert power. For instance, an acoustic repeater may receive the transcutaneous power with a first diaphragm. In this scenario, the received power may then be retransmitted via a second diaphragm. In accordance with the techniques described herein, the second diaphragm may be smaller than the first diaphragm. The smaller size may be better matched to the bodily tissue 302 between the repeater and the electronic device 106 than the larger size. The larger size may be better matched to the bodily tissue 302 (e.g., the skin 304) and air between the wireless power transmitter 108 and the repeater. The deep link may also be implemented using a wired coupling. This is another example of how the signal characteristics be adjusted by the conductive tattoo 104.

FIG. 4 illustrates an example configuration in which an injected conductive tattoo receives power wirelessly from a transmitter outside the body and has a wired coupling to an implanted electronic device in accordance with one or more aspects at 400. The depicted configuration of FIG. 4. also includes the conductive tattoo 104, the electronic device 106, and the wireless power transmitter 108. Like the depicted configuration of FIG. 3, the depicted configuration of FIG. 4 includes bodily tissue 402 with skin 404.

In contrast to FIG. 3 though, the example configuration depicted in FIG. 4 represents a scenario in which the deep link is implemented via wired coupling 406. In particular, the example configuration represents a scenario in which the power wirelessly received by the conductive tattoo 104, from the wireless power transmitter 108, is supplied to the electronic device 106 across the wired coupling 406. By way of example, the wired coupling 406 may correspond to a wire or conductor that is surgically implanted into the person 102 and is capable of supplying power from the conductive tattoo 104 to the electronic device 106.

Figure 5:
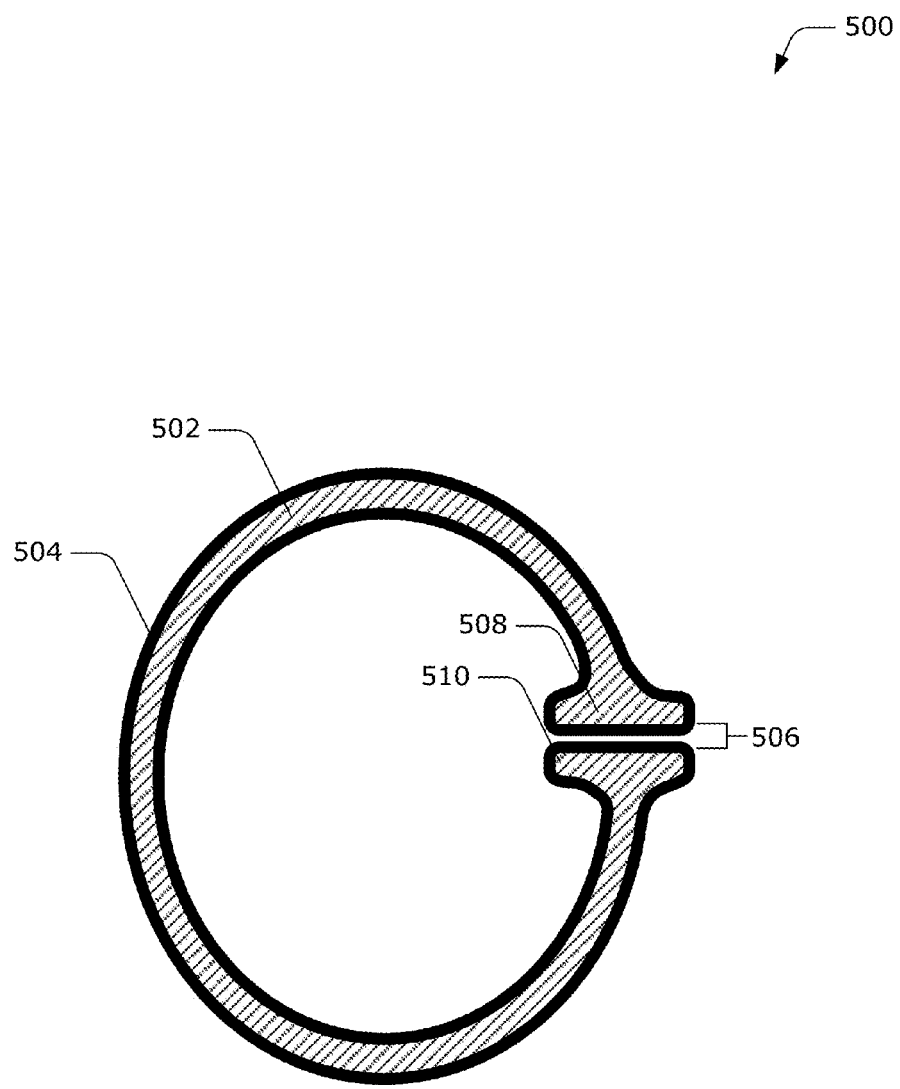
FIG. 5 illustrates an example pattern in which the injected conductive tattoo can be applied.

FIG. 5 illustrates an example pattern in which the injected conductive tattoo can be applied in accordance with one or more aspects at 500. The conductive particles 214 may be injected into the skin in a variety of different patterns to form the conductive tattoo 104. By way of example, a simple loop pattern may enable the conductive tattoo 104 to receive power and reradiate the power deeper into the body to the electronic device 106.

In particular, the example pattern depicts a simple resonant loop 502 with insulating loop 504. The simple resonant loop 502 forms a capacitor based on a gap 506 between wide terminations 508, 510 of a conductive trace. Injecting the conductive particles 214 in this pattern is effective to form an inductor and a capacitor. The capacitance of the formed capacitor can be adjusted by changing a width of the gap 506, changing a length of each conductive edge of the wide terminations 508, 510, and so forth. By widening the edges and bringing them closer together, for instance, capacitance can be increased. This allows a person applying the conductive particles 214 into the skin to tune the conductive tattoo 104 during application. The capacitance that is created by configuring the conductive tattoo 104 as a capacitor enables the conductive tattoo to be tuned to a particular frequency or impedance, e.g., for relaying power deeper into the body to the electronic device 106. In general, the simple resonant loop 502 may be configured to resonate at a frequency of a field generated by the wireless power transmitter 108, e.g., a magnetic field. In response to the transmitter-generated magnetic field, the simple resonant loop 502 is configured to generate a magnetic field, and transmits power to the electronic device 106 via the generated magnetic field.

The insulating loop 504 may be applied by injecting into the skin insulating ink that comprises non-conductive or minimally conductive particles, e.g., acrylic or latex based ink. In aspects, the insulating loop 504 may be applied in a band around the conductive tattoo 104, such as in a band around the simple resonant loop 502. The insulating loop 504 can serve as insulation to prevent particles of the conductive tattoo 104 from migrating through the skin over time. In this way, the insulating loop 504 can be used to maintain the gap 506 between the wide terminations 508, 510. It should be appreciated that a thickness of the insulating loop 504 may vary in some aspects and may be relatively consistent in others. Further, the ink used for the insulating loop 504 may vary in color, such that in some aspects the insulating loop 504 may be visible to the human eye while in others it is not visible to the human eye. In some alternate aspects, non-conductive ink may not be applied to form the insulating loop 504. In any case, applying the conductive particles 214 to the skin in the simple resonant loop 502 may be useful in repeater applications, where the power signal from the wireless power transmitter 108 is repeated to the electronic device 106.

Figure 6:
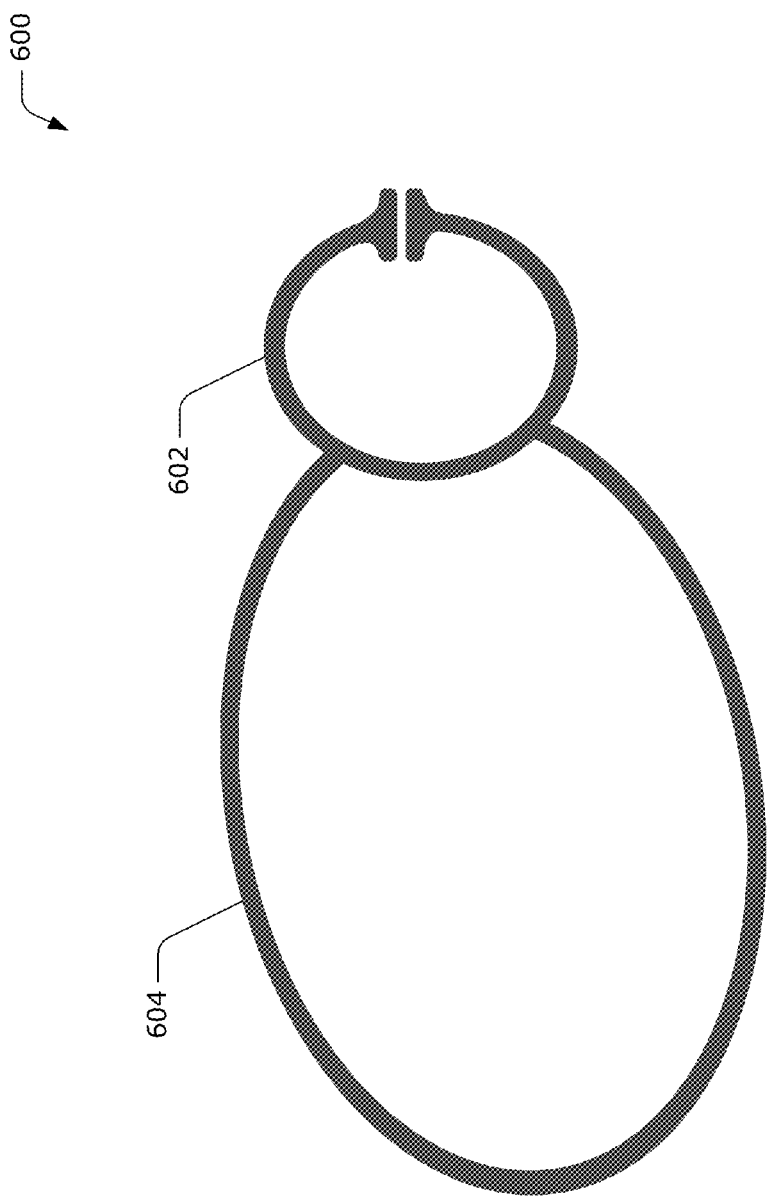
FIG. 6 illustrates another example pattern in which the injected conductive tattoo can be applied.

FIG. 6 illustrates another example pattern in which the injected conductive tattoo can be applied in accordance with one or more aspects at 600. In particular, the example pattern depicts a gamma loop resonant structure that includes smaller resonant loop portion 602 and larger resonant loop portion 604. The gamma loop resonant structure may be formed by injecting the conductive particles 214 in the skin to form the smaller resonant loop portion 602 and the larger resonant loop portion 604 around the smaller resonant loop portion 602. The larger resonant loop portion 604 may be connected around the smaller resonant loop portion 602, such that the larger resonant loop portion 604 is formed with a portion of the smaller resonant loop portion 602, as illustrated.

The gamma loop resonant structure can be used to tune the conductive tattoo 104 to different impedances. For instance, the gamma loop resonant structure can transform a wireless signal from a region of low impedance to a region of high impedance, e.g., to match the power retransmitted to the electronic device 106 to operational criteria of its components. In general, the smaller resonant loop portion 602 matches to a lower impedance than the larger resonant loop portion 604. Although the conductive tattoo 104 may have a pattern corresponding to those depicted in FIGS. 5 and 6, the conductive tattoo 104 may also be applied in different patterns without departing from the spirit or scope of the techniques described herein.

Figure 7:
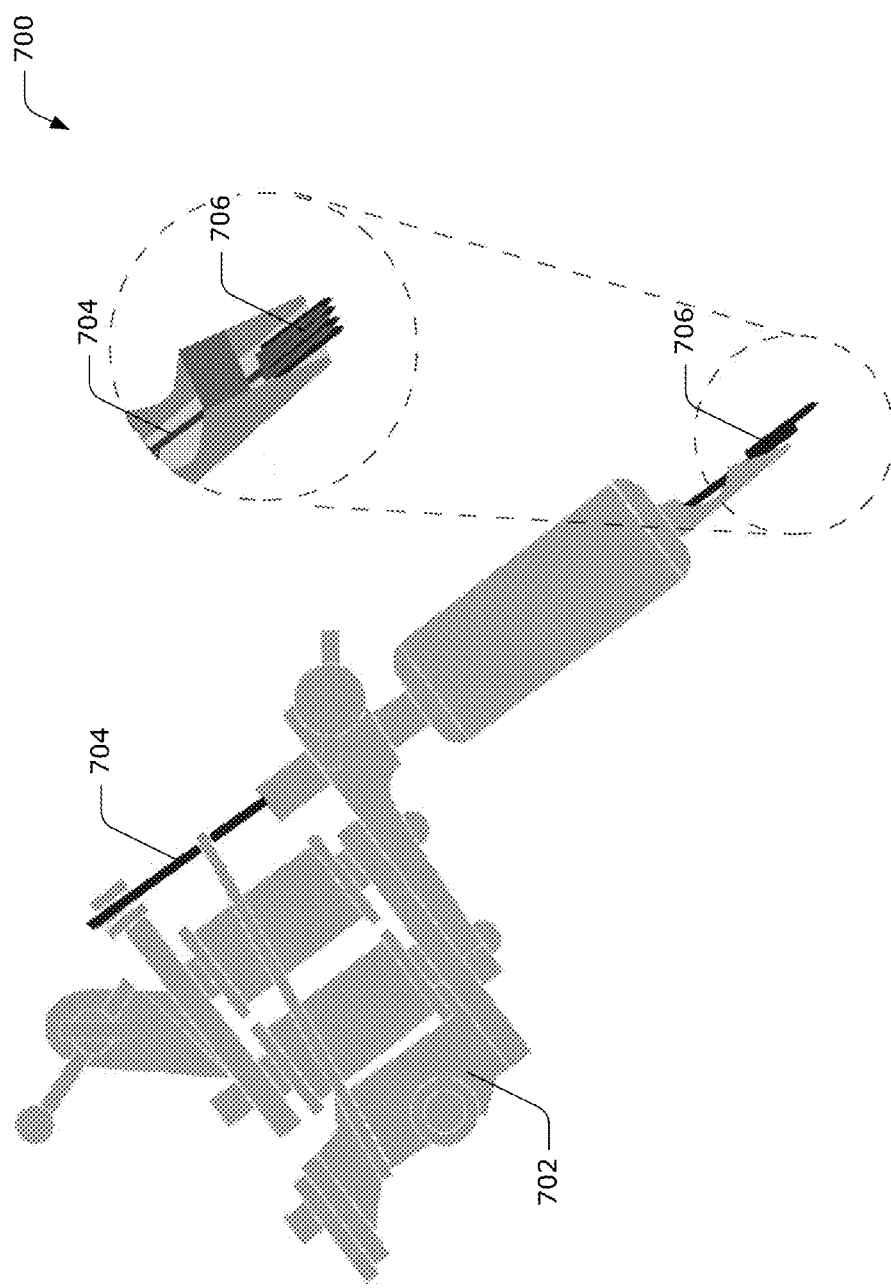
FIG. 7 illustrates an example configuration of a device that is usable to apply an injected conductive tattoo.

In this context, FIG. 7 illustrates an example configuration of a device that is usable to apply an injected conductive tattoo in accordance with one or more aspects at 700.

In particular, the illustrated example depicts tattoo machine 702. The tattoo machine 702 represents functionality to apply (e.g., inject) the conductive particles 214 to the skin to form the conductive tattoo 104. The tattoo machine 702 includes needle bar 704 and needles 706. In one or more aspects, the tattoo machine 702 is configured as a coil-based machine, a rotary machine, or another machine capable of rapidly moving the needles 706 in and out of the skin to apply the conductive particles 214.

The needle bar 704 is configured to hold the needles 706 and transfer motion of the tattoo machine 702 to the needles 706 for application of the conductive tattoo 104. The needles 706 represent functionality to hold a conductive solution (e.g., the conductive particles 214 and solution in which the particles are suspended) and transfer the conductive solution by repeatedly piercing the skin and injecting the conductive solution. Regarding the solution in which the conductive particles are suspended, it is capable of interstitial placement through capillary action. This allows the conductive solution to be placed in the person 102's skin (e.g., the dermis 204) using known tattooing techniques.

In the depicted example, the needles 706 are arranged in a seven mag configuration having three flat on four flat. Although illustrated in this configuration the needles 706 may be arranged in a variety of different configurations (e.g., having one to n needles, arranged in round, flat, oval, mag or other configurations) without departing from the spirit or scope of the techniques described herein. Regardless of the particular configuration, the needles 706 may soak up the conductive solution using capillary action. This capillary action may be similar to the manner in which a quill pen fills with ink. In single-needle arrangements, surface tension holds the conductive solution—although such arrangements hold less than is held by the multi-needle arrangements, resulting in the needle being dipped more often into the conductive solution than the multi-needle arrangements.

Figure 8:
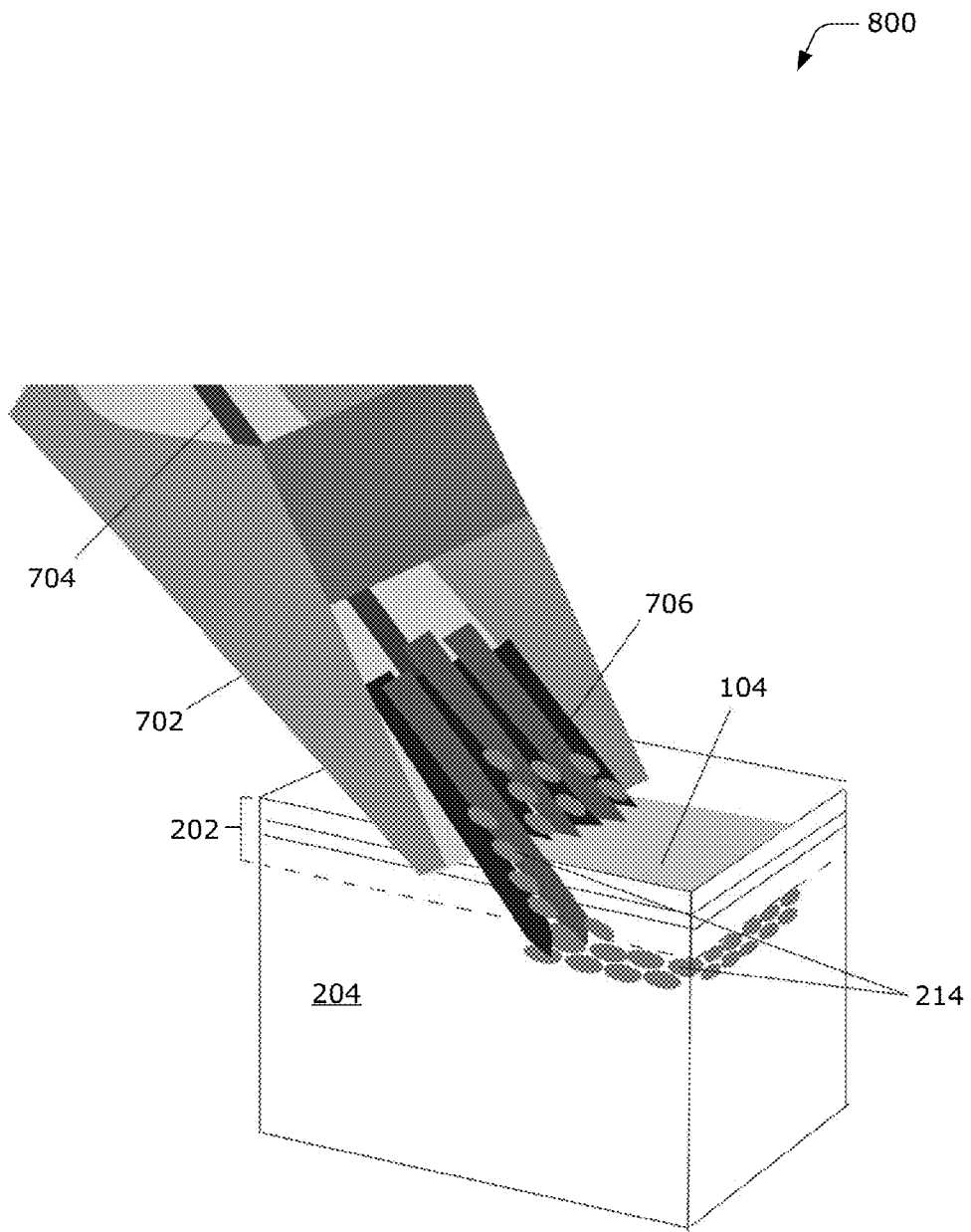
FIG. 8 illustrates an example scenario in which the device of FIG. 7 is used to apply an injected conductive tattoo to skin.

FIG. 8 illustrates an example scenario in which the device of FIG. 7 is used to apply an injected conductive tattoo to skin in accordance with one or more aspects at 800. The example scenario depicts portions of the tattoo machine 702, including the needle bar 704 and the needles 706. The example scenario also depicts portions of the cross-sectional view of the skin of FIG. 2, such as the epidermis 202 and the dermis 204. The conductive particles 214 and the conductive tattoo 104 as seen through the skin are also depicted.

In the example scenario, some of the conductive particles 214 are depicted on the needles 706 of the tattoo machine 702. This represents functionality of the tattoo machine 702 to soak up the conductive solution for application into the skin. By way of example, the needles 706 may be dipped into the conductive solution, and the space between the needles 706 may soak up the conductive solution via capillary action.

In general, the tattoo machine 702 is configured to rapidly move the needle bar 704 to apply the conductive solution, e.g., up and down rapidly with a coil machine, round and round rapidly with a rotary machine, and so on. As the needle bar 704 is brought to the surface of the skin, the motion of the tattoo machine 702 drives tips of the needles 706 into the skin to a depth of the dermis 204, which is about 2-4 millimeters below an outermost surface of the skin.

By applying the conductive solution to the skin in this manner, the conductive particles 214 are deposited at each depth along the path of the needles 706. In other words, the conductive particles 214 are disposed at depths from the outermost layer of skin to the dermis 204. The process of driving the tips of the needles 706 into the skin to apply the conductive solution is repeated while moving the tattoo machine 702 across the surface of the skin in the desired pattern, such as one of the patterns depicted in FIGS. 5-6. This forms the configuration of the conductive tattoo 104.

Over time, the conductive particles 214 injected into the epidermis 202 are expelled from the body as the outer layers of skin die and fall off. Consequently, solely the conductive particles 214 injected into the dermis 204 remain permanently in the body, thereby forming the conductive tattoo 104. Additionally, biological processes of the body encase the conductive particles 214 in specialized cells called fibroblasts. The fibroblasts keep the conductive particles 214 in place within the dermis 204. In addition, some of the conductive particles 214 are encapsulated and held in place by specialized immune system cells called macrophages. This enables the conductive tattoo 104 to couple with the wireless power transmitter 108 when placed on the surface of the skin above the conductive tattoo 104.

Like with decorative ink tattoos, the conductive tattoo 104 may wear over time. In general, the conductive particles 214 will remain in place as long as their size is greater than a size of particle that can be swept away by the lymph system— about 12 microns. When the conductive particles 214 are greater than 12 microns in size, the fibroblasts may keep them in place indefinitely. However, some conditions may break down the conductive particles 214. One example condition is sun exposure, although others may also break down the conductive particles 214. When the conductive particles 214 break down, biological processes may flush the broken-down particles out of the skin and deposit them in the lymph nodes. This can cause the conductive tattoo 104 to lose some conductivity. If the loss of conductivity degrades the ability of the conductive tattoo 104 to receive and transmit power, the conductive tattoo 104 can be touched up. To do so, conductive particles can be injected into the skin again over the existing conductive tattoo 104 to add more conductive particles.

In some scenarios it may be desirable to remove the conductive tattoo 104, such as when the person 102 no longer uses the electronic device 106. Such scenarios may arise when an implant is removed or the implant has performed its corresponding functionality and is no longer needed. In these scenarios, the conductive tattoo 104 can be removed by using a laser to break down the conductive particles 214. The laser may be capable of breaking down the conductive particles 214 to a size the lymph system is capable of removing from the skin. Nonetheless, if the person 102 no longer uses the electronic device 106, the conductive tattoo 104 may also safely remain in place without harming the person 102.

Techniques of Injected Conductive Tattoos for Powering Implants

The following techniques of injected conductive tattoos for powering implants may be implemented using any of the previously described conductive tattoos of the example environment. The techniques may also involve powering an implant configured like the electronic device 106 of the example environment or the system-on-chip described with reference to FIG. 11. Reference to entities, such as the conductive tattoo 104 or the electronic device 106, is made by example only and is not intended to limit the ways in which the techniques can be implemented. The techniques are described with reference to example methods illustrated in FIGS. 9 and 10. The example methods are depicted as respective sets of operations or acts that may be performed using the entities described herein and/or any suitable components which provide means for implementing one or more of the operations. The depicted sets of operations illustrate a few of the many ways in which the techniques may be implemented. As such, operations of a method may be repeated, combined, separated, omitted, performed in alternate orders, performed concurrently, or used in conjunction with another method or operations thereof.

Figure 9:
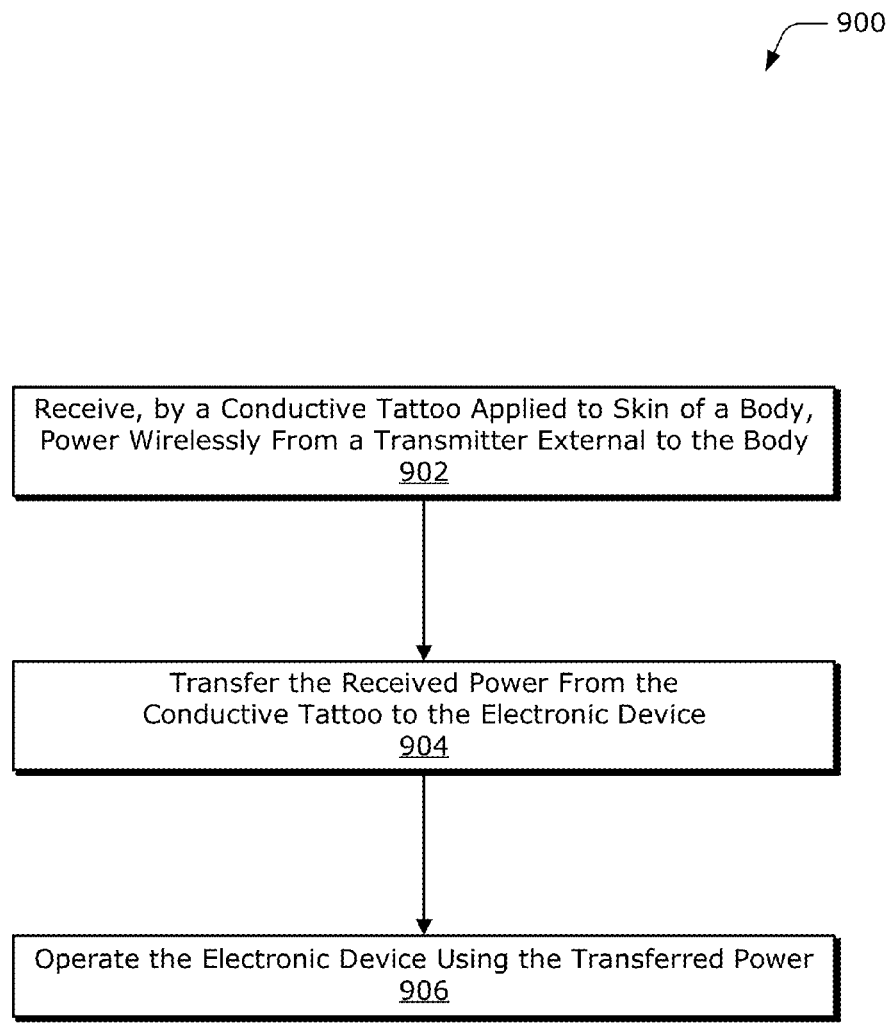
FIG. 9 illustrates an example method for powering an implant using an injected conductive tattoo.

FIG. 9 illustrates an example method 900 of powering an implant using an injected conductive tattoo, including operations performed by the conductive tattoo 104. In the following discussion, the conductive tattoo 104 or other entities of example environment 100 may provide means for implementing one or more of the operations described.

At 902, the method includes receiving, by a conductive tattoo applied to skin of a body, power wirelessly from a transmitter external to the body. By way of example, the conductive tattoo 104 is applied to skin of the person 102's body using the techniques described above and below. Further, the conductive tattoo 104 receives power wirelessly from the wireless power transmitter 108. The conductive tattoo 104 receives the power, for instance, when the wireless power transmitter 108 is placed on the person 102's skin proximate to the conductive tattoo 104. In scenarios in which the conductive tattoo 104 is easily visible, the wireless power transmitter 108 can be placed on the person 102's skin where the conductive tattoo 104 is visible through the skin.

In connection with the conductive tattoo 104 receiving the power, the wireless power transmitter 108 transmits the power wirelessly. The wireless power transmitter 108 may transmit the power wirelessly such that the transmission signal has a variety of different characteristics. Transmission with the different characteristics may be effective to supply the conductive tattoo 104 with power having different voltages, different waveforms (e.g., alternating current (AC), direct current (DC), pulsating DC), and so forth.

At 904, the method includes transferring the received power from the conductive tattoo to the electronic device. By way of example, the power received by the conductive tattoo 104 at 902 is transferred to the electronic device 106. The power is transferred from the conductive tattoo 104 to the electronic device 106 via a coupling, such as via one or more of the wireless coupling 306 or the wired coupling 406.

At 906, the method includes operating the electronic device using the transferred power. By way of example, the electronic device 106 carries out the functionality for which it is designed using the power received over the wireless coupling 306 or the wired coupling 406. When the electronic device 106 is an implant for releasing metered doses of medication, for instance, a metered dose of medication is released. Alternately, the electronic device 106 stimulates bodily tissue (e.g., nerves), monitors specific biochemical conditions, and so forth. Although this method step is described with reference to operations performed by biomedical implants, the operations for some implants may correspond to non-medical functionality, such as location tracking, data storage/communication, personal information access, and so on.

Figure 10:
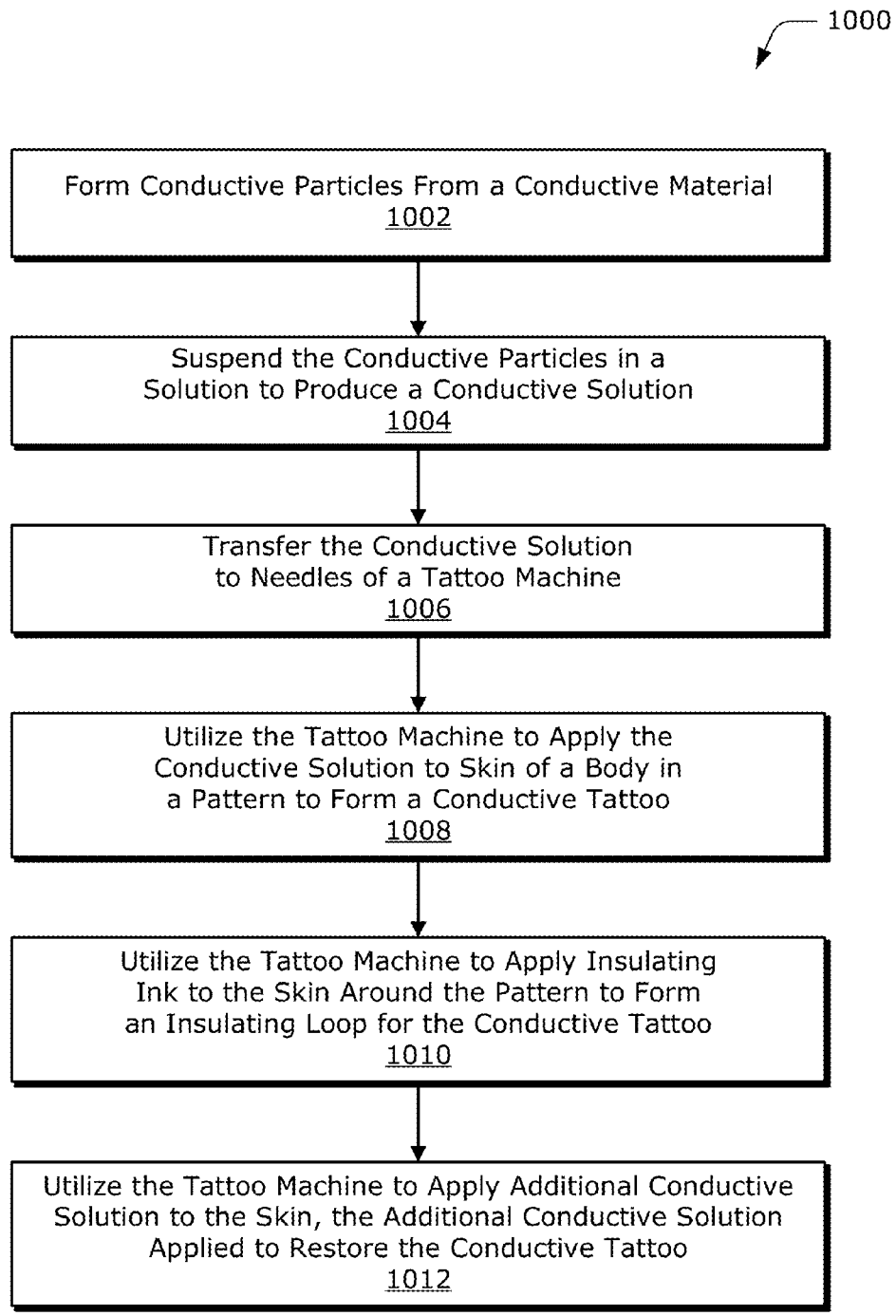
FIG. 10 illustrates an example method for applying an injected conductive tattoo to skin for powering an implant.

FIG. 10 illustrates an example method 1000 of applying an injected conductive tattoo to skin for powering an implant. In the following discussion, the tattoo machine 702 and its components may provide means for implementing one or more of the operations described.

At 1002, the method includes forming conductive particles from a conductive material. By way of example, the conductive particles 214 are formed by grinding down a conductive material so that the resulting particles have a size of approximately 13-14 microns. At 1004, the method includes suspending the conductive particles in a solution to produce a conductive solution. By way of example, the conductive particles 214 formed at 1002 are suspended in a transparent solution (e.g., saline, water, plasma) to achieve a mildly visible or unnoticeable conductive tattoo. Alternately, the conductive particles 214 formed at 1002 are suspended in a colored solution (e.g., black or colored decorative tattoo ink) to achieve a conductive tattoo that is easily visible to the human eye. Regardless of the solution in which the conductive particles 214 are suspended, the suspension produces a conductive solution. This conductive solution is usable by the tattoo machine 702 to apply the conductive tattoo 104 to the person 102.

At 1006, the method includes transferring the conductive solution to needles of the tattoo machine. By way of example, the conductive solution produced at 1004 is transferred to the needles 706 of the tattoo machine 702. In aspects, the needles 706 are dipped into the conductive solution, and the space between the needles 706 soaks up the conductive solution via capillary action.

At 1008, the method includes applying the conductive solution with the tattoo machine to skin of a body. In accordance with the aspects described herein, the tattoo machine applies the conductive solution to the skin in a pattern to form a conductive tattoo. By way of example, the conductive solution is applied to skin of the person 102 using the tattoo machine 702. Further, the tattoo machine 702 is used to apply the conductive solution to the skin in a pattern to form the conductive tattoo 104, such as the patterns depicted in FIGS. 5-6. In one or more aspects, the tattoo machine 702 applies the conductive solution by rapidly moving the needle bar 704. This drives the tips of the needles 706 into the skin to a depth of the dermis 204, where the conductive solution is deposited. The biological processes discussed above encase the conductive particles 214 of the conductive solution. This keeps them in place indefinitely—like ink of a traditional, decorative tattoo—forming the conductive tattoo 104.

At 1010, the method includes applying insulating ink with the tattoo machine to the skin. In accordance with one or more aspects, the tattoo machine applies the insulating ink around the pattern to form an insulating loop for the conductive tattoo. By way of example, the insulating ink is applied to skin of the person 102 using the tattoo machine 702. Further, the tattoo machine 702 is used to apply the insulating ink to the skin around the pattern in which the conductive solution is applied at 1008. In this way, an insulating loop is formed for the conductive tattoo 104, such as the insulating loop 504.

At 1012, the method includes applying additional conductive solution to the skin with the tattoo machine to restore the conductive tattoo. As described in more detail above, the conductive tattoo 104 may wear over time, e.g., due to sun damage. In scenarios where the wear affects the ability of the conductive tattoo 104 to wirelessly receive power and retransmit the power to the electronic device 106, additional conductive solution can be applied to restore the conductive tattoo 104. By way of example, the additional conductive solution is applied to the skin of the person 102 using the tattoo machine 702 to restore the conductive tattoo 104. The additional conductive solution can be produced via acts 1002 and 1004.

Although acts 1008-1012 are described with reference to the tattoo machine 702, it should be appreciated that different tattoo machines may be used for the different acts. Likewise, multiple different tattoo machines may be used for a single act. Conductive solution may be applied using multiple different tattoo machines to form the conductive tattoo 104 in a variety of different scenarios, for example, such as when a tattoo machine breaks, multiple applications of conductive ink at different times are used to form the conductive tattoo 104, and so forth.

System-on-Chip

Figure 11:
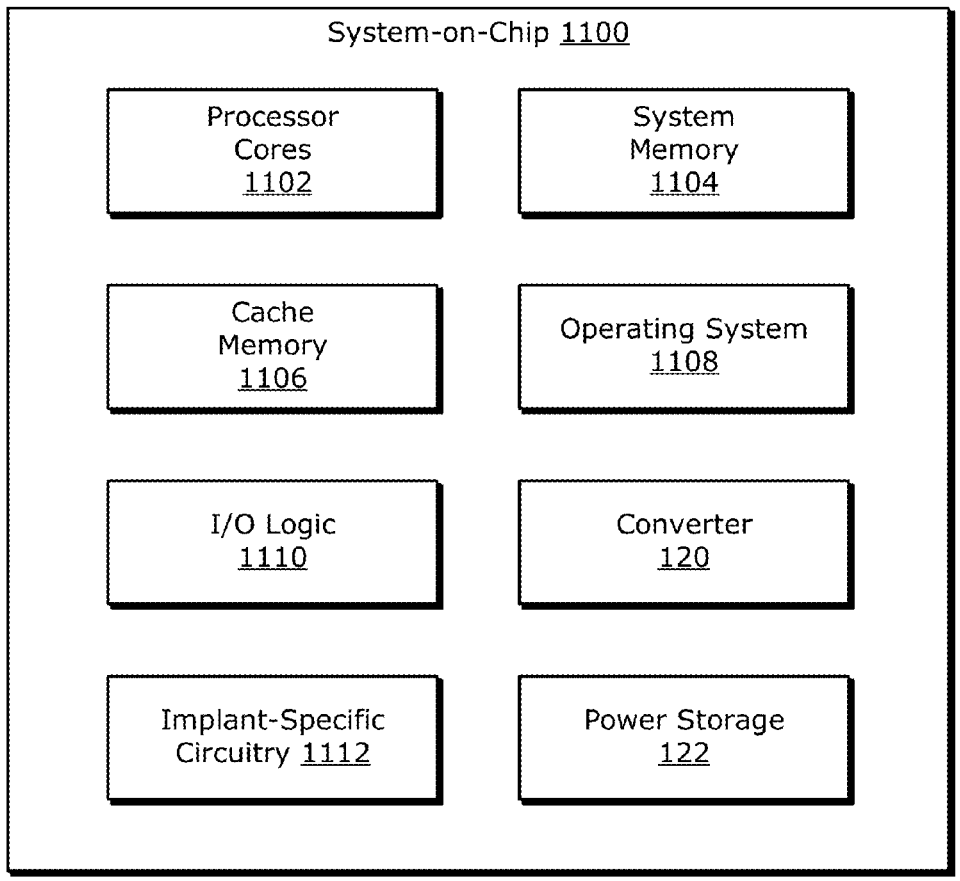
FIG. 11 illustrates a system-on-chip (SoC) having components through which aspects of injected conductive tattoos for powering implants can be implemented.

FIG. 11 illustrates an example system-on-chip 1100, which includes components capable of implementing aspects of injected conductive tattoos for powering implants. The system-on-chip 1100 may be implemented as, or in, any suitable electronic device, such as implants to carry out corresponding functionality or any other device that may utilize power transmitted to it from an injected conductive tattoo.

The system-on-chip 1100 may be integrated with, a microprocessor, storage media, I/O logic, data interfaces, logic gates, a transmitter, a receiver, circuitry, firmware, software, or combinations thereof to provide communicative or processing functionalities. The system-on-chip 1100 may include a data bus (e.g., cross bar or interconnect fabric) enabling communication between the various components of the system-on-chip. In some aspects, components of the system-on-chip 1100 may interact via the data bus to implement aspects of injected conductive tattoos for powering implants.

In this particular example, the system-on-chip 1100 includes processor cores 1102, system memory 1104, and cache memory 1106. The system memory 1104 or the cache memory 1106 may include any suitable type of memory, such as volatile memory (e.g., DRAM), non-volatile memory (e.g., Flash), and the like. The system memory 1104 and the cache memory 1106 are implemented as a storage medium, and thus do not include transitory propagating signals or carrier waves. The system memory 1104 can store data and processor-executable instructions of the system-on-chip 1100, such as operating system 1108 and other applications. The processor cores 1102 execute the operating system 1108 and other applications from the system memory 1104 to implement functions of the system-on-chip 1100, the data of which may be stored to the cache memory 1106 for future access. The system-on-chip 1100 may also include I/O logic 1110, which can be configured to provide a variety of I/O ports or data interfaces for inter-chip or off-chip communication.

The system-on-chip 1100 also includes the converter 120, the power storage 122, and implant-specific circuitry 1112, which may be embodied separately or combined with other components described herein. For example, a power receiving unit, including the power storage 122 and/or the converter 120 as described with reference to FIG. 1, may be integral with the injected conductive tattoo 104 through a coupling. The implant-specific circuitry 1112 can be implemented to carry out functionality specific to an implant.

The implant-specific circuitry 1112 may also be integrated with other components of the system-on-chip 1100, such as the cache memory 1106, a memory controller of the system-on-chip 1100, or any other signal processing, modulating/demodulating, or condition sections within the system-on-chip 1100. The implant-specific circuitry 1112 and other components of the system-on-chip 1100 may be implemented as hardware, fixed-logic circuitry, firmware, or a combination thereof that is implemented in association with the I/O logic 1110 or other signal processing circuitry of the system-on-chip 1100.

Wireless Power Transfer System

Figure 12:
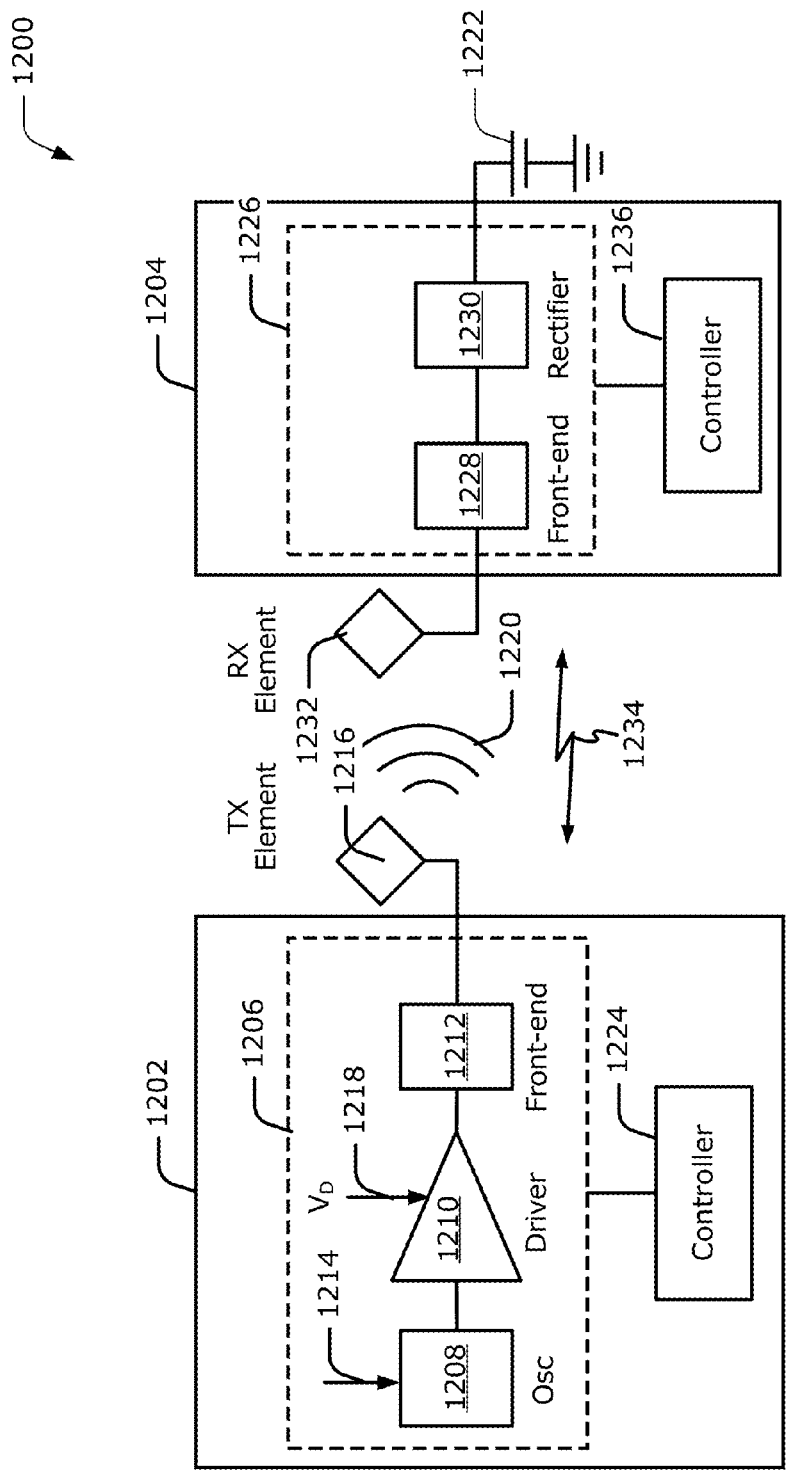
FIG. 12 illustrates a wireless power transfer system having components through which aspects of injected conductive tattoos for powering implants can be implemented.

FIG. 12 illustrates an example wireless power transfer system 1200, which includes components capable of implementing aspects of injected conductive tattoos for powering implants. The system 1200 includes a transmitter 1202 and a receiver 1204. The transmitter 1202 may include transmit circuitry 1206 having an oscillator 1208, a driver circuit 1210, and a front-end circuit 1212. The oscillator 1208 may be configured to generate an oscillator signal at a desired frequency that may adjust in response to a frequency control signal 1214. The oscillator 1208 may provide the oscillator signal to the driver circuit 1210. The driver circuit 1210 may be configured to drive the power transmitting element 1216 at, for example, a resonant frequency of the power transmitting element 1216 based on an input voltage signal (VD) 1218. The driver circuit 1210 may be a switching amplifier configured to receive a square wave from the oscillator 1208 and output a sine wave.

The front-end circuit 1212 may include a filter circuit configured to filter out harmonics or other unwanted frequencies. The front-end circuit 1212 may include a matching circuit configured to match the impedance of the transmitter 1202 to the impedance of the power transmitting element 1216. The front-end circuit 1212 may include also a tuning circuit to create a resonant circuit with the power transmitting element 1216. As a result of driving the power transmitting element 1216, the power transmitting element 1216 may generate a wireless field 1220 to wirelessly output power at a level sufficient for charging a battery 1222, or otherwise powering a load.

The transmitter 1202 may further include a controller 1224 operably coupled to the transmit circuitry 1206 and configured to control one or more aspects of the transmit circuitry 1206, or accomplish other operations relevant to managing the wireless transfer and powering an implant with an injected conductive tattoo. The controller 1224 may be a micro-controller or a processor. The controller 1224 may be implemented as an application-specific integrated circuit (ASIC). The controller 1224 may be operably connected, directly or indirectly, to each component of the transmit circuitry 1206. The controller 1224 may be further configured to receive information from each of the components of the transmit circuitry 1206 and perform calculations based on the received information. The controller 1224 may be configured to generate control signals (e.g., the control signal 1214) for each of the components that may adjust the operation of that component. As such, the controller 1224 may be configured to adjust or manage the power transfer for powering an implant with an injected conductive tattoo based on a result of the operations it performs. The transmitter 1202 may further include a memory (not shown) configured to store data, for example, such as instructions for causing the controller 1224 to perform particular functions, such as those related to management of wireless power transfer.

The receiver 1204 may include receive circuitry 1226 having a front-end circuit 1228 and a rectifier circuit 1230. The front-end circuit 1228 may include matching circuitry configured to match the impedance of the receive circuitry 1226 to the impedance of the power receiving element 1232. The front-end circuit 1228 may further include a tuning circuit to create a resonant circuit with the power receiving element 1232 and/or the injected conductive tattoo 104. The rectifier circuit 1230 may generate a DC power output from an AC power input to charge the battery 1222, as shown in FIG. 7, or provide power to some other load. The receiver 1204 and the transmitter 1202 may additionally communicate on a separate communication channel 1234, e.g., Bluetooth™, ZigBee™, and cellular. The receiver 1204 and the transmitter 1202 may alternatively communicate via in-band signaling using characteristics of the wireless field 1220.

Further, the receiver 1204 may be configured to determine whether an amount of power transmitted by the transmitter 1202 and received by the receiver 1204 is appropriate for charging the battery 1222 or powering a load. In certain embodiments, the transmitter 1202 may be configured to generate a predominantly non-radiative field with a direct field coupling coefficient (k) for providing energy transfer. The receiver 1204 may directly couple to the wireless field 1220 and may generate an output power for storing or consumption by the battery 1222 (or load), coupled to the output of the receive circuitry 1226. The receiver 1204 may also be capable of coupling to a repeated wireless field produced by the injected conductive tattoo 104.

The receiver 1204 may further include a controller 1236 configured similarly to the transmit controller 1224 as described above for one or more wireless power management aspects of the receiver 1204. The receiver 1204 may further include a memory (not shown) configured to store data, such as instructions for causing the controller 1236 to perform particular functions, such as those related to management of wireless power transfer and powering an implant with an injected conductive tattoo. The transmitter 1202 and receiver 1204 may be separated by a distance and configured according to a mutual resonant relationship to minimize transmission losses between the transmitter 1202 and the receiver 1204.

The power transmitting element 1216 and the power receiving element 1232 may correspond to or be included as part of, respectively, the wireless power transmitter 108 and the power receiving unit 116 that utilize injected conductive tattoos for powering implants described herein.

Although subject matter has been described in language specific to structural features or methodological operations, it is to be understood that the subject matter defined in the appended claims is not necessarily limited to the specific features or operations described above, including not necessarily being limited to the organizations in which features are arranged or the orders in which operations are performed.

What is claimed is:

1. A system for transferring power wirelessly received from a transmitter located outside a body to an electronic device in the body, the system comprising:
    a conductive tattoo formed from a conductive material injected into an outermost permanent layer of the body and configured to wirelessly receive the power from the transmitter and transmit the power via a coupling to the electronic device.

2. The system as recited in claim 1, wherein the conductive material is injected in a pattern to form the conductive tattoo, the pattern comprising a resonant loop with an inductor and capacitor.

3. The system as recited in claim 2, wherein the resonant loop is configured to resonate at a frequency of a field generated by the transmitter.

4. The system as recited in claim 2, wherein the resonant loop is configured to generate a magnetic field in response to a transmitter-generated magnetic field and inductively couple with the electronic device using the magnetic field to transmit the power.

5. The system as recited in claim 1, wherein the conductive material is injected in a pattern to form the conductive tattoo, the pattern comprising a gamma loop resonant structure.

6. The system as recited in claim 5, wherein the gamma loop resonant structure comprises a smaller resonant loop with a capacitor, the gamma loop resonant structure further comprising a larger resonant loop formed with a portion of the smaller resonant loop, and the larger resonant loop configured to tune the gamma loop resonant structure to a different impedance for transferring the power.

7. The system as recited in claim 6, wherein the smaller resonant loop is configured to match a lower impedance than the larger resonant loop.

8. The system as recited in claim 1, wherein the conductive material is injected in a loop to form the conductive tattoo, the loop configured to allow current to flow around the loop.

9. The system as recited in claim 1, wherein the outermost permanent layer of the body is dermis of the body's skin.

10. The system as recited in claim 1, further comprising an insulating loop formed from insulating ink injected into the body around the conductive tattoo to prevent the conductive material from migrating through the body.

11. The system as recited in claim 1, wherein the conductive material comprises particles having a size of 13-14 microns.

12. The system as recited in claim 1, wherein the conductive material is an inorganic conductive material comprising at least one of copper, gold, silver, carbon, or titanium oxide.

13. The system as recited in claim 1, wherein the conductive material is injected into the outermost permanent layer of the body using a tattoo machine capable of applying ink tattoos.

14. The system as recited in claim 1, wherein the coupling is a wired coupling between the conductive tattoo and the electronic device.

15. The system as recited in claim 1, wherein the coupling is a wireless coupling between the conductive tattoo and the electronic device.

16. The system as recited in claim 1, wherein the conductive tattoo is visible to a human eye on the body's skin.

17. The system as recited in claim 1, wherein the conductive tattoo is not visible to a human eye on the body's skin.

18. A method for transferring power wirelessly received from a transmitter located outside a body to an electronic device in the body, the method comprising:
    receiving, by a conductive tattoo applied within the body's skin, the power wirelessly from the transmitter; and
    transferring the power from the conductive tattoo to the electronic device.

19. The method as recited in claim 18, further comprising operating the electronic device using the transferred power.

20. The method as recited in claim 18, further comprising transferring the power via a wireless coupling between the conductive tattoo and the electronic device.

21. The method as recited in claim 20, wherein the wireless coupling is formed by generating a magnetic field through which the power is inductively transferred from the conductive tattoo to the electronic device.

22. The method as recited in claim 18, further comprising transferring the power via a wired coupling between the conductive tattoo and the electronic device.

23. The method as recited in claim 18, further comprising preventing, by an insulating loop applied within the body's skin around the conductive tattoo, conductive particles of the conductive tattoo from migrating out of a pattern in which the conductive tattoo is applied.

24. A method for applying a conductive tattoo that transfers power wirelessly received from a transmitter located outside a body to an electronic device in the body, the method comprising:
    forming conductive particles from a conductive material;
    suspending the conductive particles in a solution to produce a conductive solution;
    transferring the conductive solution to a tattoo machine; and
    applying the conductive solution into the skin of the body with the tattoo machine in a pattern to form the conductive tattoo, the conductive particles disposed in the pattern enabling the conductive tattoo to receive power transmitted wirelessly from the transmitter and transfer the power to the electronic device.

25. The method as recited in claim 24, wherein:

the conductive solution is transferred to needles of the tattoo machine via capillary action; and applying the conductive solution with the tattoo machine includes injecting the conductive solution into the skin via the needles.

26. The method as recited in claim 24, wherein the conductive solution is injected into at least a dermis of the skin effective to cause one or more biological processes of the body to encase the conductive particles in at least one of fibroblasts or macrophages.

27. The method as recited in claim 24, further comprising applying insulating ink to the skin around the conductive tattoo to form an insulating loop that prevents the conductive particles from migrating out of the pattern, the insulating ink being applied with the tattoo machine or at least one other tattoo machine.

28. A system for transferring power wirelessly transmitted from outside a body to power an implant in the body, the system comprising:

a power-transferring means for transferring the power wirelessly transmitted by a transmitter means outside the body to a power-receiving means in the body, the power-transferring means embedded in a permanent layer of the body; and one or more implant-function means for carrying out corresponding functionality of the implant in the body using the power transferred to the power-receiving means.

29. The system as recited in claim 28, further comprising a power conversion means for converting the power received from the power-transferring means for use by the one or more implant-function means.

30. The system as recited in claim 28, wherein the power-receiving means is configured to receive the power from the power transferring means over at least one of a wireless coupling or a wired coupling.

* * * * *